(12) United States Patent
Leckrone et al.

(10) Patent No.: US 8,475,468 B2
(45) Date of Patent: Jul. 2, 2013

(54) METHOD AND APPARATUS FOR PROVIDING INTRA-PERICARDIAL ACCESS

(75) Inventors: Michael E. Leckrone, Mahtomedi, MN (US); Timothy G. Laske, Shoreview, MN (US); Michael Ujhelyi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1572 days.

(21) Appl. No.: 10/606,909

(22) Filed: Jun. 26, 2003

(65) Prior Publication Data

US 2004/0024435 A1 Feb. 5, 2004

Related U.S. Application Data

(62) Division of application No. 09/430,096, filed on Oct. 29, 1999, now Pat. No. 6,613,062.

(51) Int. Cl.
*A61F 11/00* (2006.01)
(52) U.S. Cl.
USPC ..................................... 606/108; 604/164.04
(58) Field of Classification Search
USPC ............. 606/108, 194, 190; 607/120; 604/46, 604/510, 164.01–165.04, 158, 93.01, 533–539; 285/80, 86, 89, 92
See application file for complete search history.

(56) References Cited

U.S. PATENT DOCUMENTS

| 1,738,996 | A | * | 12/1929 | Hamilton et. al. | 285/93 |
|---|---|---|---|---|---|
| 3,645,562 | A | * | 2/1972 | Fandetti et al. | 285/73 |
| 3,721,229 | A | | 3/1973 | Panzer | 128/2 A |
| 4,682,981 | A | * | 7/1987 | Suzuki et al. | 604/158 |
| 4,946,457 | A | | 8/1990 | Elliott | 606/1 |
| 4,991,578 | A | | 2/1991 | Cohen | |
| 5,146,925 | A | | 9/1992 | Snow | 128/658 |
| 5,269,326 | A | | 12/1993 | Verrier | |
| 5,330,496 | A | | 7/1994 | Alferness | |
| 5,336,252 | A | * | 8/1994 | Cohen | 607/119 |
| 5,344,439 | A | | 9/1994 | Otten | 607/126 |
| 5,345,927 | A | | 9/1994 | Bonutti | |
| 5,415,637 | A | | 5/1995 | Khosravi | |
| 5,454,790 | A | | 10/1995 | Dubrul | 604/104 |

(Continued)

FOREIGN PATENT DOCUMENTS

WO WO 97/42879 11/1997

*Primary Examiner* — Darwin Erezo

(57) ABSTRACT

A method and apparatus for accessing the pericardial space which provides for stable short term or long term placement of a delivery catheter or cannula having its distal most end located in the pericardial space. The catheter or cannula may be introduced into the pericardial space either transvenously through the wall of a heart chamber or transthoracically by penetrating the chest wall and the pericardium. Some embodiments are provided with a mechanism for stabilizing the distal end of the catheter or cannula, which mechanism may employ an extensible elastic, generally tubular member located at the distal end of the catheter or cannula. The device may be provided with a mechanism for extending the tubular member longitudinally, causing its diameter to diminish substantially. The tubular member may be passed through the wall of the heart or the pericardium in its extended configuration and thereafter, the distal-most portion of the tubular member may be moved proximally, causing its diameter enlarge, anchoring the distal end of the catheter or cannula to the pericardium or to the wall of a heart chamber. In these embodiments, the device is preferably provided with a shoulder or flange located proximal to the extendible tubular member, for location on the opposite side of the heart wall or pericardium from the distal end of the catheter or cannula.

5 Claims, 15 Drawing Sheets

U.S. PATENT DOCUMENTS

| | | |
|---|---|---|
| 5,489,270 A | 2/1996 | Van Erp |
| 5,531,780 A * | 7/1996 | Vachon ......................... 607/120 |
| 5,672,158 A * | 9/1997 | Okada et al. ............... 604/164.1 |
| 5,678,572 A | 10/1997 | Shaw et al. |
| 5,681,280 A | 10/1997 | Rusk et al. |
| 5,713,867 A | 2/1998 | Morris |
| 5,749,883 A | 5/1998 | Halpern |
| 5,759,202 A | 6/1998 | Schroeppel .................. 607/126 |
| 5,797,870 A | 8/1998 | March et al. |
| 5,800,451 A | 9/1998 | Buess et al. ................... 606/185 |
| 5,827,216 A | 10/1998 | Igo et al. |
| 5,928,260 A | 7/1999 | Chin et al. |
| 6,066,149 A | 5/2000 | Samson et al. |
| 6,187,023 B1 * | 2/2001 | Bonutti ......................... 606/190 |
| 6,203,526 B1 | 3/2001 | McBeth et al. ............ 604/96.01 |
| 6,375,668 B1 | 4/2002 | Gifford et al. |
| 6,692,458 B2 * | 2/2004 | Forman et al. ............. 604/93.01 |

* cited by examiner

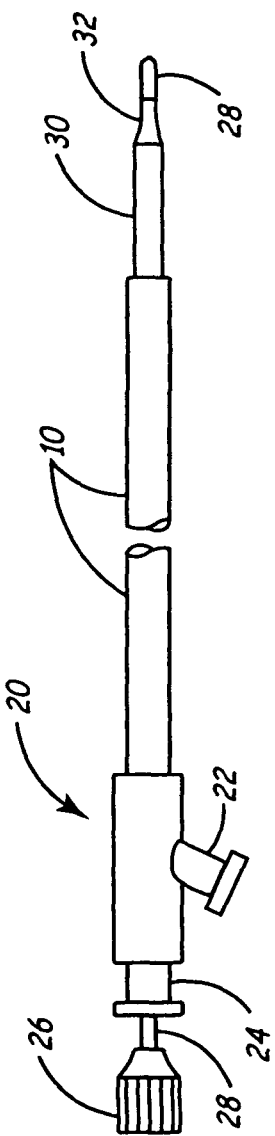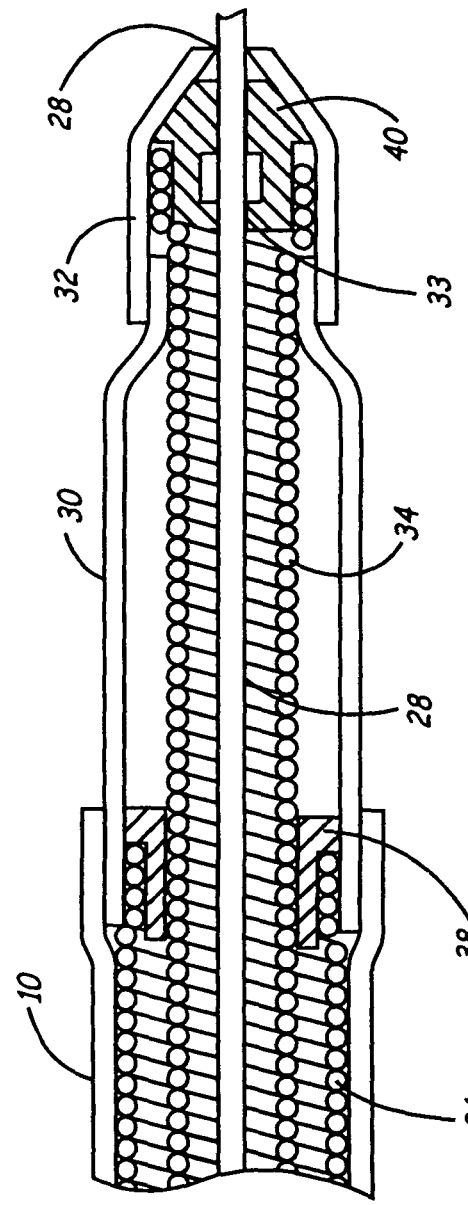

METHOD AND APPARATUS FOR PROVIDING INTRA-PERICARDIAL ACCESS

CROSS-REFERENCE TO RELATED APPLICATIONS

This application is a division of application Ser. No. 09/430,096, filed Oct. 29, 1999, now U.S. Pat. No. 6,613,062.

BACKGROUND OF THE INVENTION

This invention relates generally to diagnostic and therapeutic devices for insertion into a patient's body, and more particularly to devices for access to and delivery of treatment in the pericardial space.

Access to the pericardial space is desirable in order to provide a variety of cardiac therapies, including delivery of drugs or genetic agents, placement of electrical leads for pacing, cardioversion, defibrillation or EGM monitoring, removal of pericardial fluid for diagnostic analysis, or other purposes. A variety of mechanisms have been developed for accessing the pericardial space, ranging from a simple puncture by means of a large bore needle to intricate catheter or cannula based systems provided with sealing and anchoring mechanisms. Access to the pericardial space may be accomplished from either outside the body, by piercing the pericardium or from inside the heart, by piercing the wall of a heart chamber.

Prior art mechanisms adapted to access the pericardial space by piercing the heart chamber include U.S. Pat. No. 5,797,870 issued to March et al, which discloses use of a transvenous catheter provided with a hollow helical needle to pierce the wall of a heart chamber. Alternatively access to the pericardial space may also be accomplished by means of a transvenous catheter which pierces the wall of a heart chamber and allows passage of a lead therethrough is disclosed in U.S. Pat. No. 4,946,457 issued to Elliot, U.S. Pat. No. 4,991, 578 issued to Cohen. and U.S. Pat. No. 5,330,496 issued to Alferness. Particularly in the context of access to the pericardial space via the right atrium, it has been proposed that the transvenous catheter pierce the right atrial wall, as in U.S. Pat. No. 4,946,457 issued to Elliot or that the catheter pierce the right atrial appendage as in U.S. Pat. No. 5,269,326 issued to Verrier. Access to the pericardial space from the exterior of the body, accomplished by passing a cannula or catheter type device through the chest wall and thereafter passing the cannula or catheter through the pericardium into the pericardial space is disclosed in U.S. Pat. No. 5,827,216 issued to Igo, U.S. Pat. No. 5,336,252 issued to Cohen and PCT Patent Application WO/99/13936, by Schmidt.

SUMMARY OF THE INVENTION

The present invention is directed toward providing a mechanism for accessing the pericardial space which provides for stable short term or long term placement of a delivery catheter or cannula having its distal most end located in the pericardial space. The catheter or cannula may be introduced into the pericardial space either transvenously through the wall of a heart chamber or transthoracically by penetrating the chest wall and the pericardium.

In particular, some embodiments of devices according to the present invention are provided with a mechanism for stabilizing the distal end of the catheter or cannula. In a first embodiment of the invention, the mechanism for stabilizing the distal portion of the catheter or cannula comprises an extensible elastic, generally tubular member located at the distal end of the catheter or cannula. The device is provided with a mechanism for extending the tubular member longitudinally, causing its diameter to diminish substantially. The tubular member is passed through the wall of the heart or the pericardium in its extended configuration and thereafter, the distal most portion of the tubular member is moved proximally, causing its diameter enlarge, anchoring the distal end of the catheter or cannula to the pericardium or to the wall of a heart chamber. In these embodiments, the device is preferably provided with a shoulder or flange located proximal to the extendible tubular member, for location on the opposite side of the heart wall or pericardium from the distal end of the catheter or cannula.

In other embodiments of the present invention, the catheter or cannula takes the form of two nested tubular members, each provided with an extensible flange. The innermost of the two tubular members is provided with one or more radially extending protrusions or recesses, which engage with one or more corresponding protrusions or recesses located on the interior surface of the outer tubular member. Preferably, a series of outwardly directed protrusions on the inner tubular member and a series of inwardly directed protrusions the outer tubular member are provided, together defining multiple detent points for stabilizing the longitudinal position of the inner and outer tubular members relative to one another. More preferably, the protrusions and indentations of the tubular members extend around less than the entire circumference of the tubular members and are arranged so that in a first configuration, the tubular members may be slid longitudinally with respect to one another without interference between the protrusions on the inner and outer tubular members and in a second configuration the protrusions on the tubular members are interlocked to prevent relative longitudinal movement. In use, the catheter or cannula is employed by first passing the distal tip of the inner tubular member through the pericardial wall or the wall of a heart chamber such that the flange located thereon is located inside the pericardial space. The outer tubular member is then moved distally relative to the new tubular member to a point where the inner and outer flanges are located on either side of the pericardium or the heart wall, and the interlocking protrusions on the inner and outer catheter are thereafter employed to stabilize the catheter by preventing further relative longitudinal movements of the inner and outer tubular members.

In addition to the delivery of drugs, extraction of pericardial fluids, and location of medical electrical leads typically as typically accomplished by means of pericardial access to devices, the devices according to the present invention may also be employed as part of a system for accomplishing cardiac ablation. In this context, after stabilization of the catheter's or cannula's distal end in the pericardial space, an ablation catheter is passed through to the catheter or cannula into the pericardial space, is located at a desired location adjacent the epicardium of the heart and is thereafter employed to ablate cardiac tissue. In this context, preferred embodiments of ablation catheters for use according to the invention are provided with one or more suction ports, allowing the distal portion of the catheter to be adhered to the surface of the epicardium by suction, along with one or more electrodes, located to contact the epicardium of the heart when the distal portion of the ablation catheter is secured to the epicardium by suction.

In additional embodiments of the invention, the catheter or cannula for accessing the pericardial space takes the form of part of an implantable lead system, in which the introducer catheter or cannula is provided with one or more electrodes adapted to be located in a desired chamber or chambers of the heart, and wherein an electrode lead is passed distally through the catheter or cannula into the pericardial space, to locate additional electrodes adjacent desired portions of the epicardium of the heart. For example, electrodes located within the chamber or chambers of the heart may include pacing, cardioversion or defibrillation electrodes, and additional such electrodes may be located on the lead passing through the catheter or cannula into the pericardial space.

BRIEF DESCRIPTION OF THE DRAWINGS

FIG. 1 is a plan view of a first embodiment of a catheter or cannula according to the present invention.

FIG. 2 is a cross-sectional view through the distal portion of the catheter or cannula of FIG. 1.

FIG. 17 illustrates a drug delivery catheter; FIG. 18 illustrates a pacing/electrogram sensing lead; FIG. 19 illustrates a cardioversion/defibrillation lead; and FIG. 20 illustrates an ablation catheter.

DETAILED DESCRIPTION OF THE PREFERRED EMBODIMENTS

Figure 3:
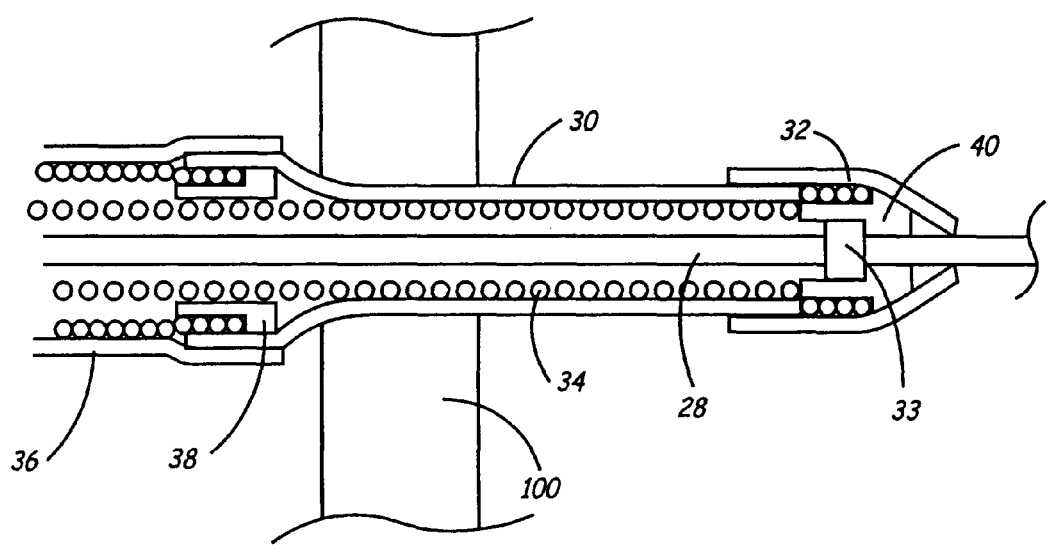
FIG. 3 is a cross-section of the distal portion of the catheter or cannula of FIG. 1, illustrating the extension of a resilient tubular member located at its distal tip, as the distal tip of the catheter or cannula is passed through the wall of a heart chamber.

FIG. 1 is a plan view of a delivery catheter or cannula according to the present invention. The catheter or cannula is provided with an elongated tubular body 10, which is provided with a fitting 20 at its proximal end which includes first and second fluid fittings 22 and 24, which may take the form of luer lock fittings. Shown entering the proximal end of fluid fitting 24 is a stylet 28, provided with a knob 26 located on its proximal portion. The distal tip of stylet 28 exits the distal tip 32 of the delivery catheter or cannula. The distal tip of the stylet 28 may be rounded or may be beveled or sharpened in order to assist passage of the distal tip 32 of the catheter or cannula through the wall of the patient's heart or through the pericardium, into the pericardial space. An elastic tubular member 30 is illustrated located at the distal end of the body 10 of the catheter or cannula, and its operation in order to anchor the distal end 32 of the catheter or cannula in the pericardial space is discussed in more detail below. If the catheter or cannula is to be used for fluid delivery, an elastic tubular plastic liner may be added, located interior to coil 34.

FIG. 2 shows a catheter or cannula of FIG. 1 in a sectional view. In this view, it can be seen that the tubular lead body 10 carries a first coil 36, terminating within a circumferential flange 38 located at the distal end of the catheter or cannula body 10, and a second coil 34 extending distally thereto through the circumferential flange 38. A resilient elastic member 30, for example fabricated of a thin tube of silicone rubber, is shown mounted to and extending from the distal end of the catheter or cannula body 10 to a distal tip member 40, illustrated in this view as being a metallic member. Tube 30 is generally cylindrical and may be tapered somewhat at its distal end as illustrated. Tube 30 is free of pre-formed corrugations but, as discussed below, will exhibit corrugations in use which will serve to stabilize the distal end of the introducer catheter or cannula in the pericardium or the wall of a chamber of a patient's heart. Surrounding the distal tip member 40 is a plastic tube 32, tapered at its distal end to provide a more atraumatic tip configuration for the catheter or cannula. In the embodiment illustrated, the stylet 28 is provided with an enlarged portion 33 which engages a corresponding internal flange in tip member 40. The stylet 28 may be moved distally with respect to the catheter or cannula to extend the tubular elastic member 30 and the associated coil 34, causing the elastic tubular member 30 to neck down tightly around coil 34. Longitudinal extension of tubular member 30 may occur prior to or after passage of the distal tip of the catheter into the pericardial space FIG. 3 illustrates the catheter or cannula of FIG. 2 with the tubular member 30 stretched elastically to a greater length than as illustrated in FIG. 2 by distal movement of stylet 28. The tubular member 30 and the distal end of the catheter or cannula extend through the wall 100 of the heart chamber into the pericardial space. In this view the effect of stretching the tubular member 30 to cause it to neck down to a reduced circumference and into close contact with coil 34 is apparent. The stretching of the tubular member 30 may be done before or after passage of the tubular member 30 through the wall 100.

Figure 4:
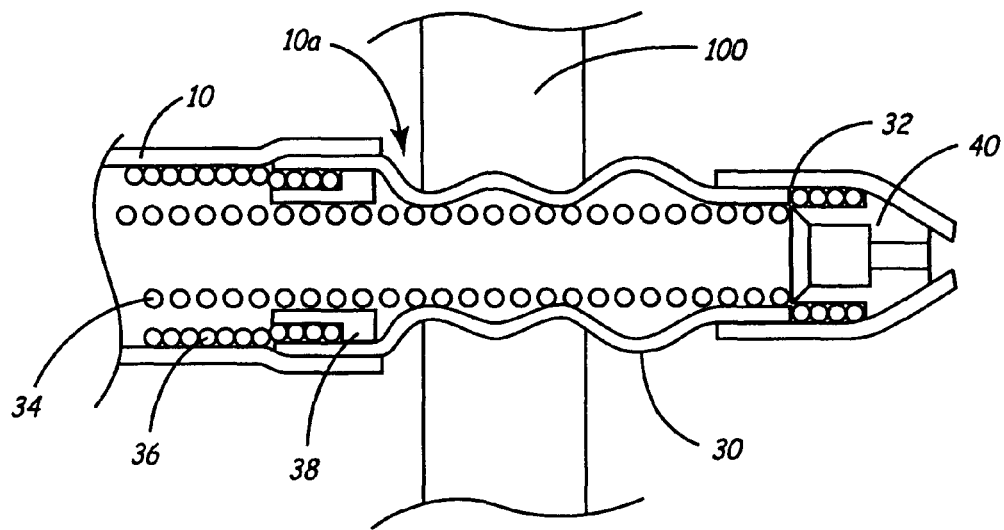
FIG. 4 illustrates the configuration of the distal end of the catheter of FIGS. 1-3, after proximal movement of the distal tip of the catheter or cannula results in lateral expansion of the resilient tubular member causing the distal tip of the catheter or cannula to be anchored within the pericardial space.

FIG. 4 illustrates the catheter or cannula of FIGS. 1-3, after removal of the stylet 28 which in turn allows for the proximal movement of the distal tip of the catheter, in turn causing expansion of the elastic tubular member 30, to anchor the distal tip of the catheter or cannula within the pericardial space. The distal end of the catheter or cannula body 10 defines a shoulder 10a on one side of the wall the heart, while the elastic member 30 forms one or more laterally extending corrugations projection located interior to the wall 100 or the pericardial space. Depending upon the relative dimensions of the heart wall 100 and the tubular member 100 and the relative amount of extensibility of the tubular member, the number and configuration of the formed corrugations may vary. The lateral expansion of the tubular member serves to anchor the distal tip of the catheter in the pericardial space. In the embodiment illustrated, it is assumed that the elasticity of coil 34 and tubular member 30 are sufficient to cause proximal movement of a distal tip of the catheter or cannula, or alternatively, that a mechanism is provided for causing proximal movement of the coil 34, facilitating proximal movement of the tip of the catheter or cannula and expansion of the tubular member 40. In such embodiments, distal movement of the coil 34 may be also employed alone or in conjunction with distal movement of the stylet to stretch the resilient tubular member 30. In additional alternative embodiments, the stylet may also be employed to cause proximal movement of the tip of the catheter or cannula, as illustrated in FIG. 5.

Figure 5:
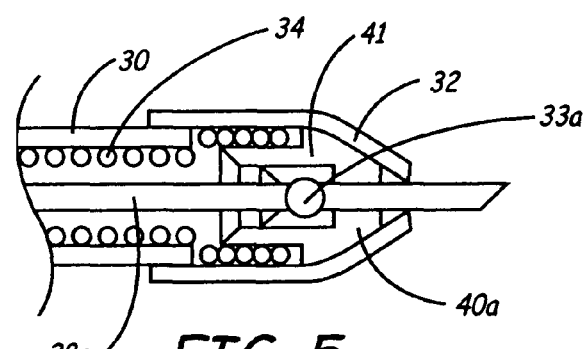
FIG. 5 is a cross-section through an alternative embodiment of a distal end portion of a catheter or cannula otherwise as illustrated in FIGS. 1-4.

FIG. 5 illustrates an alternative configuration for the distal tip portion of the catheter or cannula illustrated in FIGS. 1-4. In this embodiment, all identically labeled components correspond to those illustrated in FIG. 4, however, in this case, the stylet differs in that the expanded portion 33a of the stylet takes the form of a ball shaped, rather than a cylindrical shaped member, and that the distal tip member 40a is provided with an elastic, generally tubular member 41, configured to elastically engage the ball shaped protrusion 32a of the stylet 28a. In a fashion analogous to that illustrated for a ball-tip stylet for causing relative proximal and distal movement of a lead as in U.S. Pat. No. 5,344,439 issued to Otten, and incorporated herein by reference in its entirety, the proximal movement of the stylet may be used to affirmatively cause proximal movement of the tip member 40, up to the limit of allowable proximal motion of the tip, and thereafter, the resiliency of the locking member 41 allows for release of the ball shaped protrusion 32a, and withdrawal of the stylet 28a. In this embodiment, as in the embodiment described above in which a coils employed to pull the distal tip of tubular member 34 proximally, the resultant length of the resilient tubular member 30 may actually less than its original length, further facilitating formation of corrugations After the catheter or cannula of FIGS. 1-4 or 5 is anchored so that its distal tip is stably located in the pericardial space, the lumen defined by the interior of coil 34 and the aperture through tip member 40 provide a path by which an additional catheter or electrode lead may be passed into the pericardial space. For example, an electrode bearing catheter employed for pacing, electrogram monitoring, cardioversion or defibrillation, may be located. Alternatively, a simple, tubular catheter may be passed into the pericardium which will allow for drug delivery adjacent the localized portion of the heart. As yet, an additional alternative, the device may be employed directly as a drug delivery catheter, by means of fluids injected either through fluid coupling 24 or 22 as illustrated in FIG. 1. As yet an additional alternative, the device may be used to deliver a cardiac ablation lead, for example corresponding to those in FIGS. 20-24 and discussed in more detail below.

Figure 6:
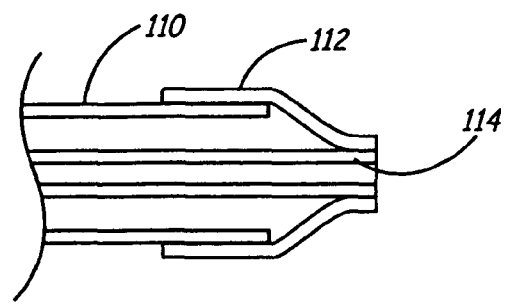
FIG. 6 is a cross-sectional view through an additional alternative embodiment of a catheter or cannula according to the present invention, also employing an extendible flexible tubular member.

FIG. 6 shows the distal portion of an alternative embodiment of a delivery catheter or cannula according to the present invention. In this embodiment, the body 110 of the device takes the form of a polymeric tube of the sort typically employed in the manufacture of guiding catheters generally, and may be reinforced by means of an embedded braid. Internal to tube 110 is a length of hypodermic tubing 114 which extends back to the proximal end of the device, and is longitudinally moveable within the lumen of tube 110. An elastic tapered tubular member 112 encircles the distal end of tube 110 and the distal end of hypodermic tube 114 and is adhesively or otherwise bonded to both tubes. In a fashion analogous to that described above in conjunction with the device of FIGS. 1-5, distal movement of hypodermic tubing 114 relative to tube 110 causes elastic member 112 to stretch and to neck down around hypodermic tube 114.

Figure 7:
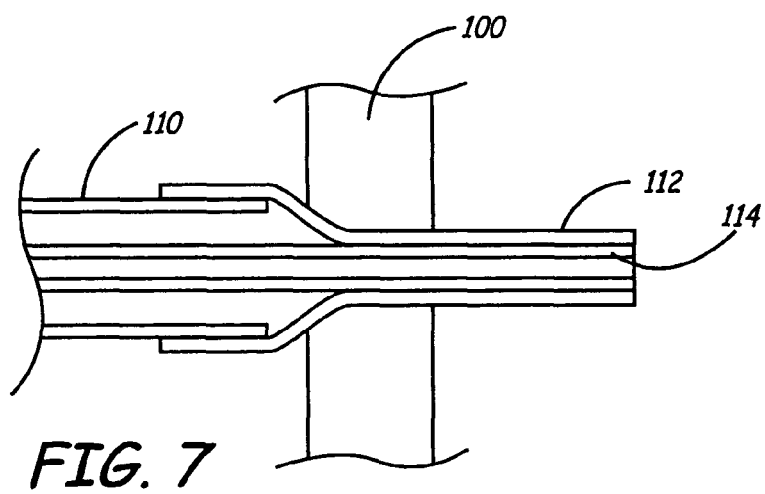
FIG. 7 illustrates the catheter or cannula of FIG. 6, having the elastic tubular member in an extended condition, as it passes through the wall of a heart chamber.

FIG. 7 illustrates the delivery catheter or cannula of FIG. 6 with hypodermic tubing 114 advanced distally out of the distal end of tube 110, stretching tubular member 112, causing it to neck down into contact with hypodermic tubing 114. The device is shown passing through the wall 100 of chamber of a patient's heart, such that the distal most portion of a hypodermic tubing 114 and tubular member 112 are located within the pericardial space.

Figure 8:
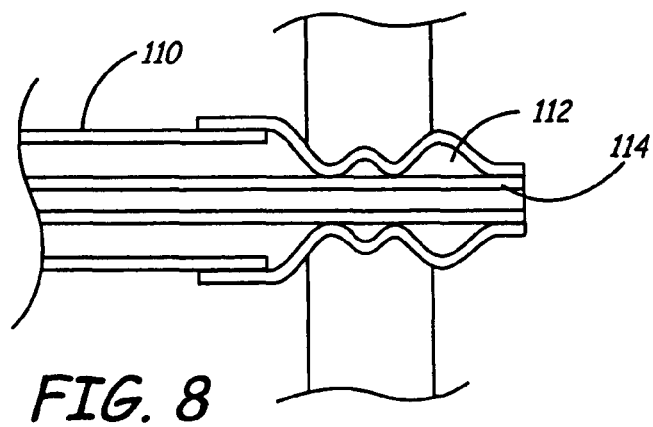
FIG. 8 illustrates the catheter of FIGS. 6 and 7 after proximal movement of the distal end of the catheter causes lateral expansion of the elastic tubular member to anchor the tip of the catheter within the pericardial space.

FIG. 8 shows the device of FIGS. 6 and 7 after the hypodermic tubing 114 is moved proximally relative to tube 110, causing elastic membrane 112 to bunch up forming one or more corrugations inside the pericardial space or in the wall 100 of a chamber of a patient's heart, stabilizing the distal end of the device within the pericardial space.

Figure 9:
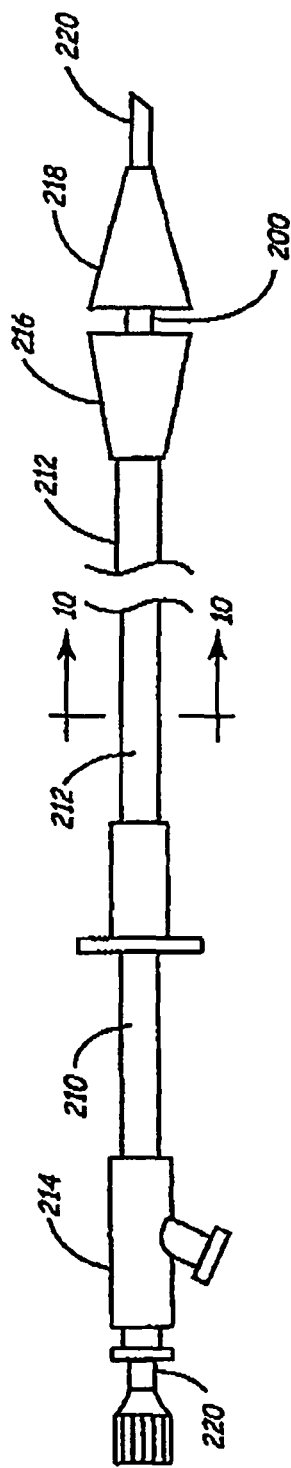
FIG. 9 is a plan view of the third embodiment of a catheter or cannula according to the present invention, employing nested inner and outer tubular members.

FIG. 9 shows an alternative embodiment of a catheter or cannula according to the present invention. In this case, the device body includes two coaxially nested tubes 210 and 212 which are slideable longitudinally with respect to one another. At the proximal end of tube 210 is a fluid fitting 212, coupled to a lumen within tube 210, and which as illustrated carries a stylet or guidewire 220, which extends out of the distal end of tube 210. The distal portion of tube 210 carries a conical flange 218, which is preferably manufactured of an elastic material such as silicone rubber and which may optionally be reinforced with radially extending ribs, if desired. The distal end of outer tube 212 has a corresponding conical flange 216, oppositely directed from flange 218.

Figure 10:
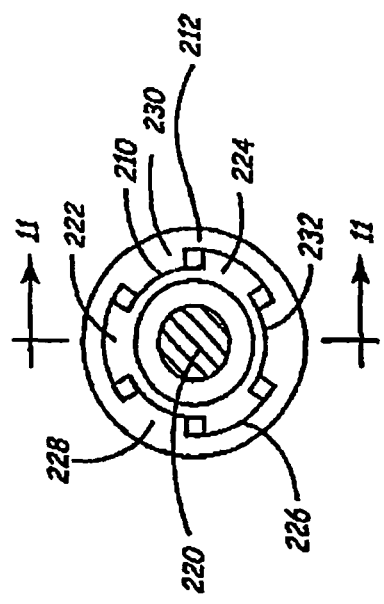
FIG. 10 is a cross-sectional view of the catheter or cannula of FIG. 9.

FIG. 10 is a cross-section through the body of the device of FIG. 9. From this view it can be seen that the outer surface of tube 210 is provided with outwardly directed projections 222, 224 and 226, which are spaced from one another around the circumference of the tube 210, and as illustrated are located displaced approximately 120° from one another. The outer surface of tube 210 is preferably provided with a series of such projections, spaced at regular intervals along a portion of tube 210. Corresponding inwardly directed projections 228, 230 and 232 are provided on the inner surface of tube 212, also spaced approximately 120° from one another. As illustrated, in the configuration shown, the projections of the respective inner and outer tubes 210 and 212 do not engage one another, allowing the tubes to be slid longitudinally. However, if the inner and outer tube are rotated 60° with respect to one another, the projections on each of the inner and outer tubes locate themselves between the projections on the other tube, causing the tubes to be interlocked and preventing further relative longitudinal movement of inner and outer tubes 210 and 212 relative to one another. This locking mechanism is employed in conjunction with stabilization of the device as discussed below.

Figure 11:
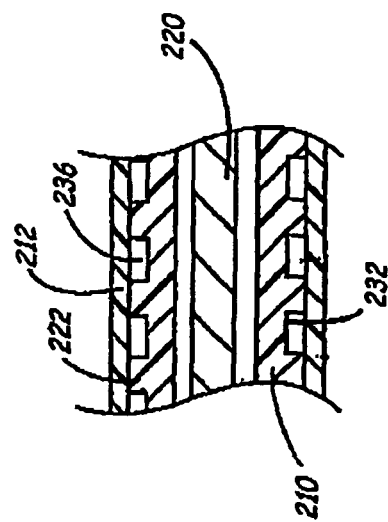
FIG. 11 is a side, sectional view through the catheter or cannula of FIGS. 9 and 10.

FIG. 11 illustrates the device of FIG. 9 in a sectional view, in which the inwardly directed projections 232 of outer tube 212 and the outwardly projected projections of tube 210 are visible. In this configuration, the tubes are free to slide longitudinally to one another. However, by rotating the tubes 60° relative to one another, the outward projections 222 of tube 210 locate themselves in the recesses 224 between the inwardly projected projections 232 of tube 212, and the inwardly directed projections 232 of tube 212 corresponding to locate themselves in the recesses 236 defined between the outward projections 222 of tube 210, preventing further longitudinal movements of tubes 210 and 212.

Figure 12:
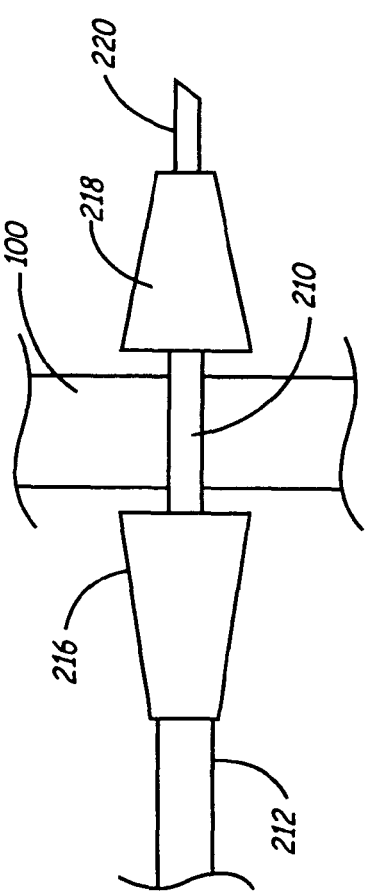
FIG. 12 illustrates placement of the catheter or cannula of FIGS. 9-11, such that the distal portion of the inner tubular member extends through the wall of the heart.

FIG. 12 illustrates the device of FIGS. 9-11 with its distal end inserted in the wall 100 in the chamber of a patient's heart. The device is positioned so that flange 218 of inner tube 210 is located within the pericardial space, while flange 216 of outer tube 212 is located interior to the patient's heart.

Figure 13:
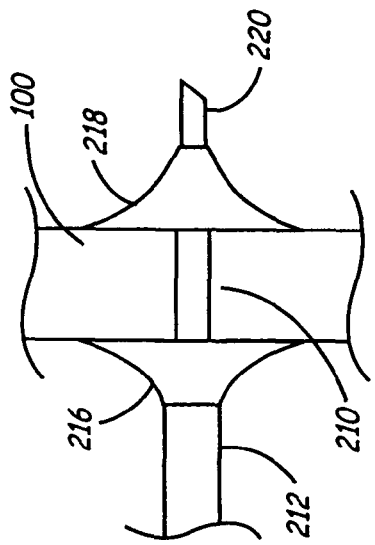
FIG. 13 illustrates the configuration of the cannula or catheter of FIGS. 9-11 after the inner and outer tubular members of the catheter or cannula are moved relative to one another to cause the flanges located thereon to engage the inner and outer surfaces of the heart, stabilizing the distal end of the catheter or cannula within the pericardial space.

FIG. 13 illustrates the device of FIG. 12 after proximal movement of tube 210 to bring flanges 216 and 218 into contact with the inner and outer surfaces of the wall 100 of the chamber of a patient's heart, also causing radial expansion of the flanges as illustrated. At this point, the inner and outer tubes are rotated relative to one another so that the inwardly and outwardly directed projections on the outer and inner tubes respectively, interlock with one another, preventing further longitudinal movement and stabilizing the distal end of the catheter in the wall 100 of the patient's heart. Stylet 220 can now be removed, and the delivery catheter or cannula may be employed to facilitate placement of a lead, catheter or other device in the pericardial space.

Figure 14:
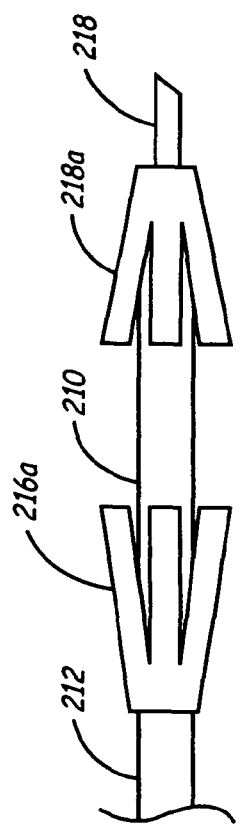
FIG. 14 illustrates an alternative embodiment of the distal portion of the catheter in FIGS. 1-11.

FIG. 14 illustrates an alternative embodiment of a delivery catheter or cannula generally corresponding to those illustrated in FIGS. 9-13. In this embodiment, however, the flanges 216a and 218a are provided with slits or recesses as illustrated in order to facilitate radial expansion of the flanges. All other elements correspond to identically labeled elements in FIGS. 9-12.

Figure 15:
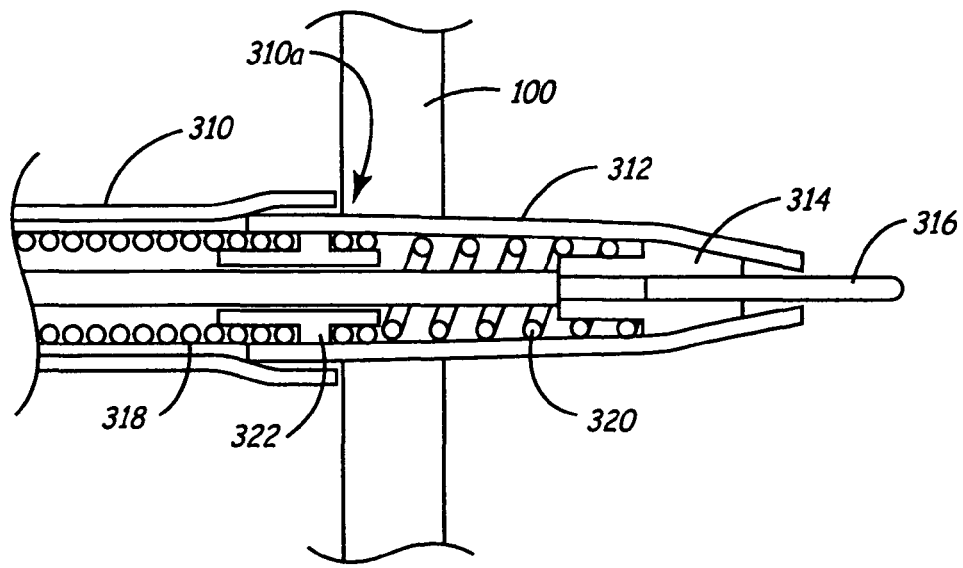
FIG. 15 illustrates a cross-sectional view of an additional embodiment of a catheter or cannula according to the present invention, employing an internal spring within a distally located elastic tubular member, illustrating the tubular member in a longitudinally extended state as it passes through the wall of a heart chamber.

FIG. 15 is an additional embodiment of a delivery catheter or cannula, according to the present invention, shown with its distal portion extending through the wall of a patient's heart. Like the devices of FIGS. 1-5, discussed above, the device is provided with a body which takes the form of a tube 310, reinforced by means of an internal coil 318. The distal end of the tube 310 serves as a radially extending shoulder 310a, which is located adjacent the inner surface of the wall 100 of a patient's heart chamber. An elastic tube 312 extends distally from tube 310 to enclose a tip member 314. Spring 320 extends from a cylindrical flange 322 to the tip member 314. As illustrated, elastic tube 312 and spring 320 have been elongated due to distal movement of stylet 316, which is provided with an outwardly directed shoulder engaging the proximal end of tip member 314.

Figure 16:
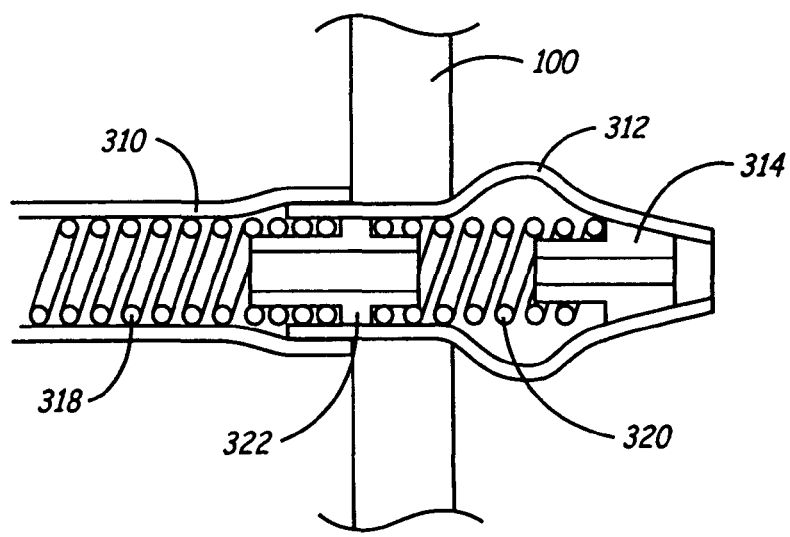
FIG. 16 illustrates the catheter or cannula of FIG. 15 after contraction of the spring located within the resilient tubular member causes lateral expansion of the resilient tubular member in the pericardial space, anchoring the distal portion of the catheter or cannula.

FIG. 16 illustrates the device of FIG. 15 after removal of stylet 316, allowing spring 320 to retract and cause radial expansion of elastic tube 312 within the pericardial space, stabilizing the distal end of the delivery catheter. All other elements correspond to identically labeled elements in FIG. 15.

FIGS. 17-24 illustrate various types of devices which may be introduced into the pericardial space using the delivery devices illustrated above. In each case, the delivery device is sized so that the lumen through the distal tip member of the delivery device is adequate to permit passage of the lead or cannula to be delivered to the pericardial space.

Figure 17:
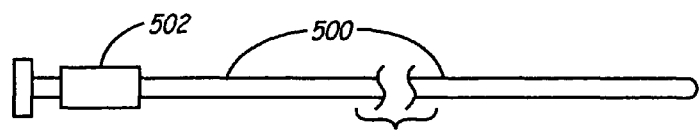
FIGS. 17-20 illustrate various types of catheters and leads which may be inserted into the pericardial space via the catheters or cannulas of FIGS. 1-16, discussed above. In particular.

FIG. 17 illustrates a simple catheter for delivery of drugs or for withdrawal of pericardial fluid. The catheter consists of a tube 500 provided with a fluid fitting 502 at its proximal end.

Figure 18:
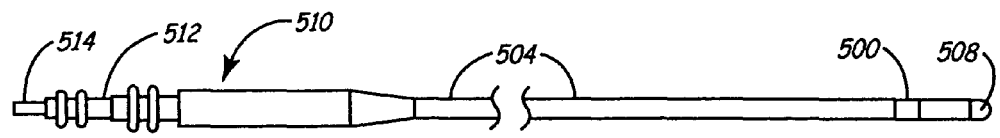

FIG. 18 illustrates an electrode lead with may be introduced through any of the delivery devices described above, and which may be employed for detection of electrical signals from the heart or delivery of electrical stimulus pulses such as pacing pulses to the heart. The lead is provided with an elongated insulative body 504 which carries two mutually insulative conductors therein coupled at their distal ends to electrodes 500 and 508, respectively, and at their proximal end to connector pin and connector ring 514 and 512, respectively. Connector pin 514 and connector ring 512 are located on a connector assembly 510 which is adapted to be inserted into the connector port of an associated electrical stimulator or monitor.

Figure 19:
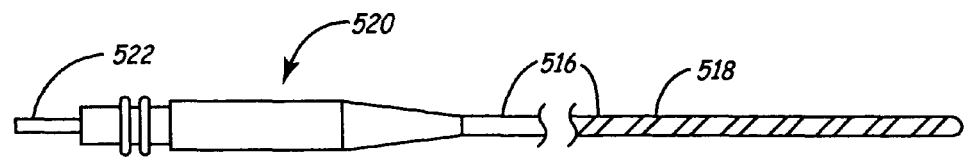

FIG. 19 illustrates a cardioversion or defibrillation lead which may be introduced by means of any of the delivery devices described above. The lead is provided with an elongated insulative lead body 516 which carries an elongated conductor coupled at its distal end to coil electrode 518 and at its proximal end to connector pin 522. Connector pin 522 is located on a connector assembly 520 adapted to be coupled to a cardioverter or defibrillator.

Figure 20:
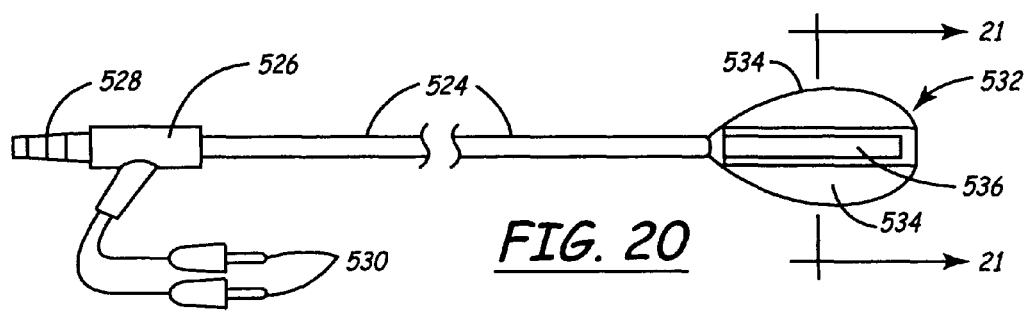

FIG. 20 illustrates an ablation catheter which may be employed in conjunction with any of the delivery devices illustrated above. The ablation catheter is provided with an elongated lead body 524 which is provided with a longitudinally extending internal lumen extending from a fluid coupling 528 at its proximal end to a longitudinally extending recess 536 at its distal end. Fluid coupling 528 is mounted to fitting 526, which also carries two electrical connectors 530, which are coupled to the distal ends of conductors 531, which extend through catheter body 524 to electrodes which are located within the recess 536, but which are not visible in this view. The distal portion 532 of the device is also provided with two laterally extending flanges 534, which serve to orient the device such that the recess 536 is located adjacent the surface of the heart tissue, as illustrated in FIGS. 21 and 22, described below.

Figure 21:
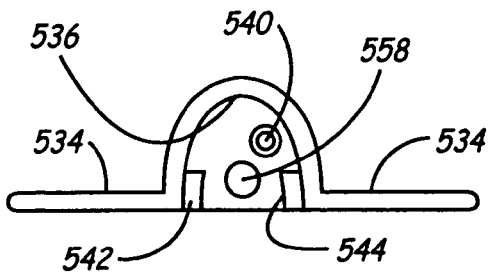
FIG. 21 illustrates a cross-section through the distal end of the ablation catheter of FIG. 20.

FIG. 21 is a cross-sectional view of the distal portion 532 of the device illustrated in FIG. 20. In this view it can be seen that the distal portion of the catheter has a portion which is generally U-shaped in cross section, defining recess 536, and carries two elongated strip electrodes 542 and 544 located on opposite sides within recess 536. Laterally extending flanges 534 are located adjacent recess 536 and serve to assure that the recess is oriented with its open portion adjacent heart tissue. Also visible is a lumen 538 which serves to couple the recess 536 to the fluid coupling 528 (FIG. 20) located at the proximal end of the lead. An optional tension wire 540 is shown which may, in some embodiments, be employed to cause deflection of the catheter, in order to facilitate its placement at a desired location on the epicardial surface of the patient's heart, using a mechanism as generally disclosed in U.S. Pat. No. 5,489,270, issued to Van Erp, incorporated herein by reference in its entirety.

Figure 22:
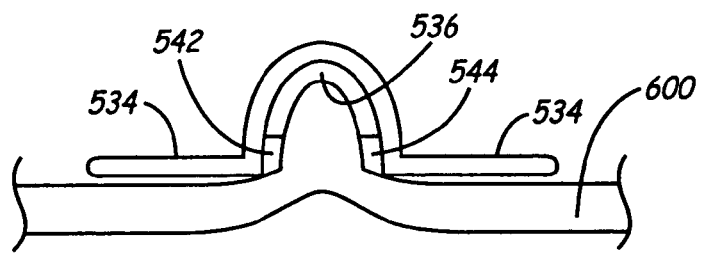
FIG. 22 illustrates the operation of an ablation catheter according to FIG. 20 or 21 to ablate heart tissue.

FIG. 22 illustrates the ablation catheter of FIGS. 20 and 21 applied to the epicardial surface of a wall 600 of a chamber of the patient's heart. Application of vacuum to the fluid fitting 528 (FIG. 20) located at the proximal portion of the catheter causes the wall 600 of the chamber of the patient's heart to be drawn into the recess 536, between electrodes 542 and 544. RF energy can then be applied to electrodes 542 and 544 via conductors 531 to create a linear lesion, extending along the length of electrodes 542 and 544.

Figure 23:
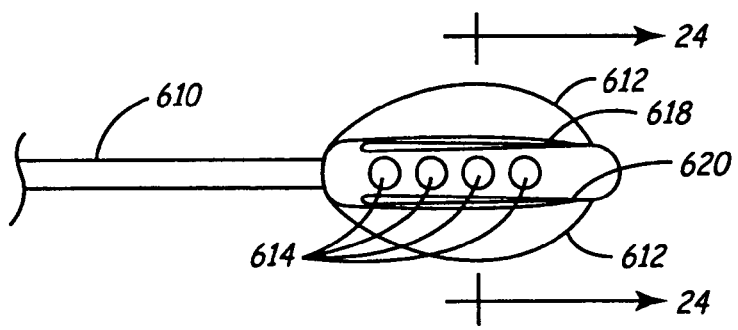
FIG. 23 illustrates an alternative embodiment of the distal portion of an ablation catheter otherwise as illustrated in FIGS. 20-22.

FIG. 23 illustrates an alternate embodiment of the distal portion of an ablation catheter otherwise corresponding to the catheter illustrated in FIGS. 21-22. In this case, it should be understood that the proximal portion of the catheter corresponds to that illustrated in FIG. 20, with catheter body 610 corresponding to catheter body 524 in FIG. 20. The distal portion of the catheter is provided with laterally extending flanges 612, corresponding generally to flanges 534. However, rather than being provided with an elongated recess, the device is provided with a longitudinal series of recesses 614. The device is also provided with two longitudinally extending electrodes 618 and 620 which may take the form of metal strips or coils, located on either side of recesses 614. Electrode 618 and 612 are coupled to electrical connectors at the proximal end of the lead, corresponding to electrical connectors 530 in FIG. 20.

Figure 24:
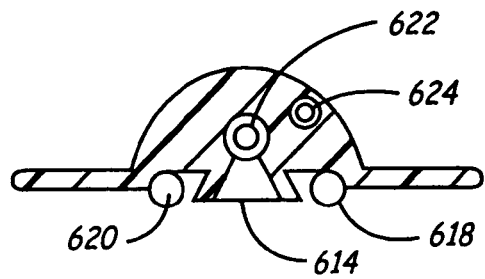
FIG. 24 illustrates a cross-section through the distal end of the ablation catheter illustrated in FIG. 23.
Figure 25:
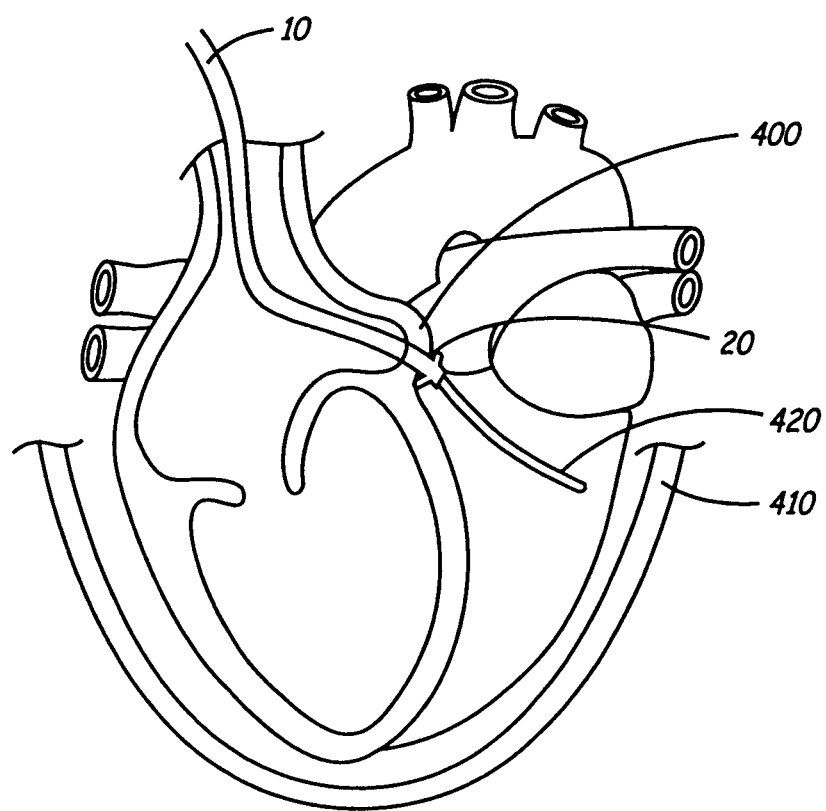
FIG. 25 illustrates a delivery catheter or cannula according to the present invention, having its distal end passing through the right atrial appendage of a patient's heart and into the pericardial space, in conjunction with a lead or catheter delivered through the introducer catheter or cannula.

FIG. 24 illustrates a cross-section through the distal portion of the ablation catheter illustrated in FIG. 23. In this view it can be seen that the recesses 614 are generally conical, and are in fluid communication with an internal lumen 624 which extends back to a fluid coupling at the proximal end of the catheter, corresponding to fluid coupling 528 in FIG. 20. Electrodes 618 and 620 are illustrated in cross-section, located on either side of recesses 614. An optional tension wire 626 is shown, which may be employed to deflect the ablation catheter assisting its location at a desired location on the epicardium of a patient's heart. In use, like the ablation catheter of FIGS. 20-22, vacuum is applied to the fluid coupling at the proximal end of the catheter, causing the suction ports 614 to adhere to the epicardial surface of a chamber of the patient's heart. RF energy is applied between electrodes 618 and 620 to create a generally linear lesion.

FIG. 24 illustrates the use of a delivery device according to the present invention to deliver a lead or catheter 420 into the pericardial space. As illustrated, it should be assumed that the delivery device corresponds to that illustrated in FIGS. 1-4, with lead body 10 extending from the superior vena cava, the distal end of the delivery device extending through the wall 400 of the right atrial appendage. As illustrated, elastic tube 20 serves to stabilize the distal end of the delivery device in the right atrial appendage and lead or catheter 420 is delivered through the distal tip of the delivery device, for location between the epicardial surface of the heart and the pericardium, illustrated schematically at 410.

Any of the delivery devices illustrated above may be employed in a corresponding fashion to deliver a lead or catheter to the pericardial space, or may be used in the absence of an associated lead or catheter to deliver materials such as drugs or genetic agents to the pericardial space or to withdraw fluid from the pericardial space. Correspondingly, devices according to any of the embodiments illustrated above may also be employed to access pericardial space by passing through the pericardium itself, with the distal end of the catheter stabilized in the pericardium, rather than in the wall of the chamber of a patient's heart.

Figure 26:
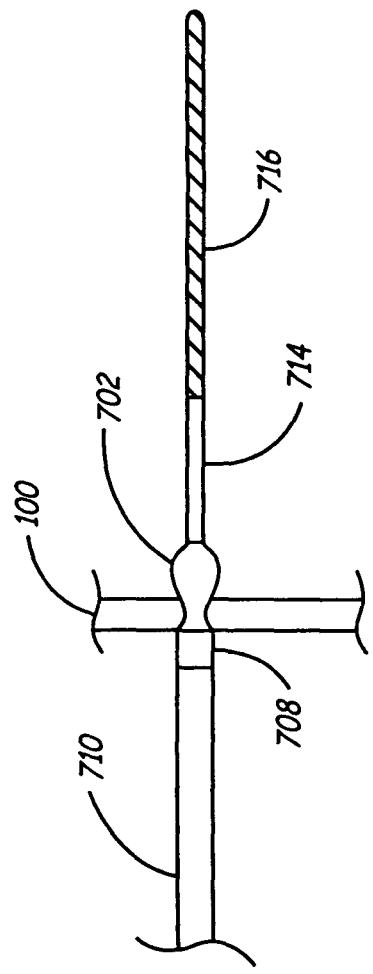
FIG. 26 illustrates the distal portion of an alternative embodiment of an introducer catheter or cannula according to the present invention, carrying one or more electrodes located along its length, in conjunction with an electrode lead delivered through the catheter or cannula into the pericardial space.

FIG. 26 illustrates an additional embodiment of a delivery device according to the present invention, wherein the delivery device is provided with an electrode 708 located at the distal portion of the tube 710, making up the catheter body. Catheter body 710 may otherwise correspond to catheter body 10 of the device illustrated in FIGS. 1-4. As illustrated, the device is shown with its distal end extending through the wall 100 of a chamber of a patient's heart, for example, extending through the right atrial appendage. Elastic tube 712 may correspond to tube 30, illustrated in FIG. 1, serving to anchor the device in the wall of the atrium in the same fashion as described in conjunction with FIGS. 1-4, above. Extending into the pericardial space is an electrode lead 714, in this case taking the form of a defibrillation lead with an elongated coil electrode 17. In an embodiment as illustrated, electrode 708 may be employed to sense or pace the atrium or other chamber of a patient's heart, with electrode 17 employed in conjunction with cardioversion or defibrillation functions. Alternatively, a lead carrying pacing and/or electrogram sensing electrodes may be substituted for lead 714, or lead 714 may be omitted, and the device simply employed to deliver drugs to the pericardial space in conjunction with pacing or monitoring the electrical activity of the patient's heart via electrode 708.

Figure 27:
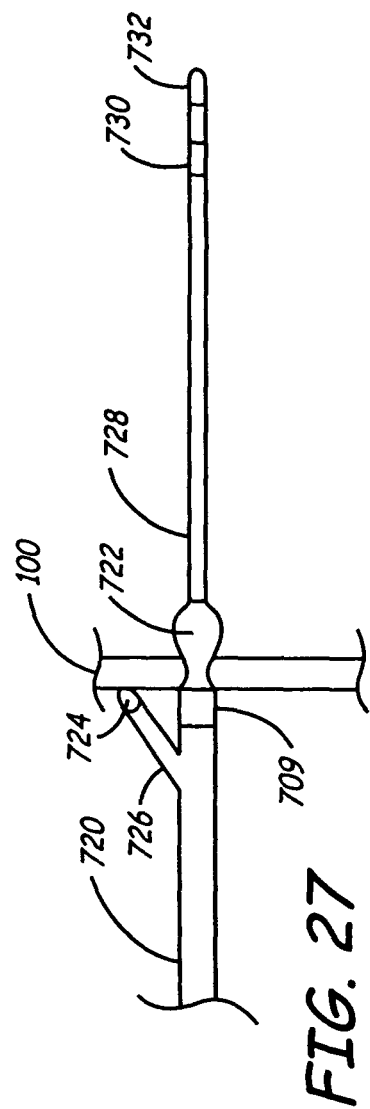
FIG. 27 illustrates the distal portion of an additional alternative embodiment of an introducer catheter or cannula according to the present invention, carrying one or more electrodes located along its length, in conjunction with an electrode lead delivered through the catheter or cannula into the pericardial space.

FIG. 27 illustrates an additional alternative embodiment to a device generally corresponding to that illustrated in FIG. 26. In this case, the device is provided with an electrode 724 located on a laterally extending arm 726 in addition to ring electrode 709 to contact the wall 100 of a chamber of a patient's heart. Catheter body 720 may correspond to the catheter body 10, as illustrated in FIGS. 1-4 above, and is stabilized in the wall 100 of a chamber of the patients heart by elastic tube 722 which also may correspond to elastic tube 30 in FIGS. 1-4. In this case, an electrode lead 228 which carries pacing/sensing electrodes 730 and 732 is shown extending into the pericardial space. As in conjunction with the device illustrated in FIG. 26, lead 728 may be replaced by a cardioversion/defibrillation lead, an ablation catheter, or may be omitted entirely.

Figure 28:
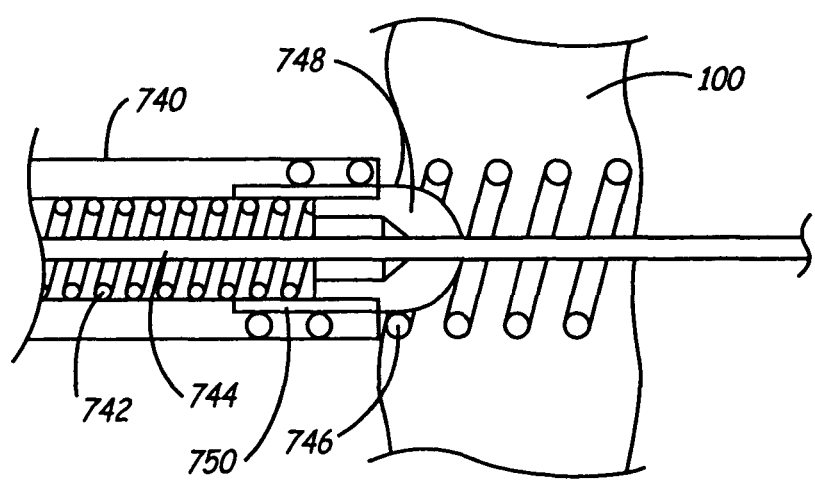
FIG. 28 illustrates the distal portion of an additional alternative embodiment of an introducer catheter or cannula according to the present invention, carrying one or more electrodes located along its length, in conjunction with an electrode lead or other catheter delivered through the catheter or cannula as it passes through a wall of a heart chamber into the pericardial space.

FIG. 28 illustrates an additional alternative embodiment of a delivery catheter or cannula 740, which is provided with a helical fixation member 746 which might also function as an electrode. Helical fixation 746 may be coupled to a coiled conductor 742 within the body of the cannula 740 by means of a conductive sleeve 750 as illustrated. In alternative embodiments, the helix 746 may merely serve to anchor the catheter or cannula 740 adjacent the wall 100 of the heart chamber. The catheter or cannula 740 is provided with a molded polymer seal 748 through which a catheter, guidewire, or electrode lead 744 passes. Seal 748 serves to seal the distal end of the delivery catheter or cannula 740 from fluid intrusion.

In cases in which the helix 746 is coupled to an internal conductor within the delivery catheter or cannula 740 and is intended to be used as an electrode, it may be used, for example, to stimulate the right atrium of the heart, with the electrode lead 744 extending therethrough passing into the pericardial space and around the heart into contact with another chamber of the heart, such as the left atrium or left ventricle of the heart.

Figure 29:
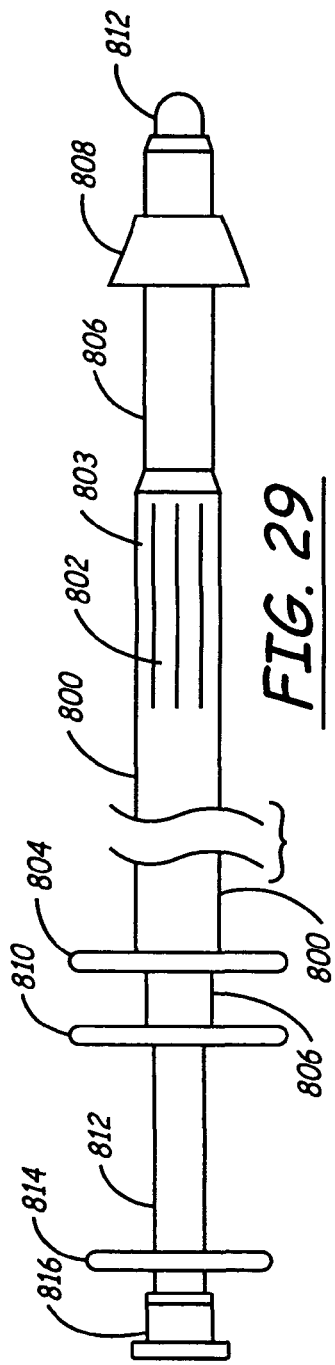
FIG. 29 illustrates the distal portion of an additional alternative embodiment of an introducer catheter or cannula according to the present invention, in conjunction with a catheter delivered through the catheter or cannula as it passes through a wall of a heart chamber into the pericardial space.
Figure 30:
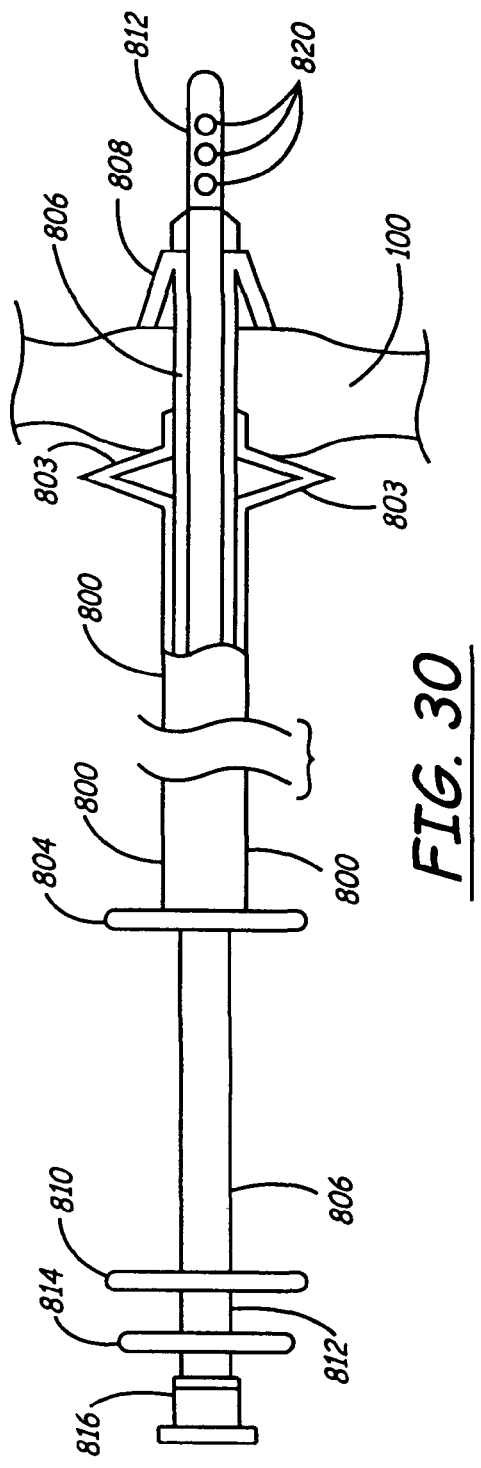
FIG. 30 illustrates the distal portion of the introducer catheter or cannula of FIG. 29, as it passes through a wall of a heart chamber into the pericardial space.

FIG. 29 illustrates an additional alternative embodiment of a delivery catheter or cannula according to the present invention. The delivery catheter or cannula comprises an outer tubular sheath 800 mounted concentrically around an inner tubular sheath 806. The outer tubular sheath 800 is provided with a series of longitudinal slots 802 which separate the outer sheath into parallel ribs which, as illustrated in FIG. 30 below, may be deflected outward to provide a mechanism for anchoring a delivery catheter or cannula adjacent one surface of a wall of a heart chamber. Inner catheter or cannula 806 is provided with a rearward facing generally conical resilient flange 808, corresponding generally to the flange 218 on the introducer catheter or cannula of FIG. 9. Inner tubular member 806 may be displaced longitudinally relative to outer tubular member 800 by means of associated handles 810 and 804. Located within inner tubular sheath 806 is a fluid delivery catheter 812, which extends out the distal end of inner tubular member 806 and is slidable longitudinally with regard to inner tubular member 806. Fluid delivery catheter 812 also has a handle 814 on its proximal end and is provided with a luer fitting 816 allowing for connection to a fluid source.

FIG. 30 illustrates the configuration of the delivery catheter or cannula of FIG. 29 as it passes through the wall 100 of a chamber of the heart. The catheter or cannula is anchored to the wall 100 of the heart by first passing the conical flange 804 of the inner tubular member 806 through the wall of the heart, thereafter advancing the outer tubular member distally until its distal end engages the wall of the heart, and then advancing the tubular member further distally, causing lateral expansion of the ribs 803 as illustrated to anchor the catheter. Tubular delivery catheter 812 may then be advanced distally the distal end of the inner tubular member 806, exposing laterally oriented delivery ports 820, which ports were previously located within and sealed by a distal portion of the inner tubular member 806.

Figure 31:
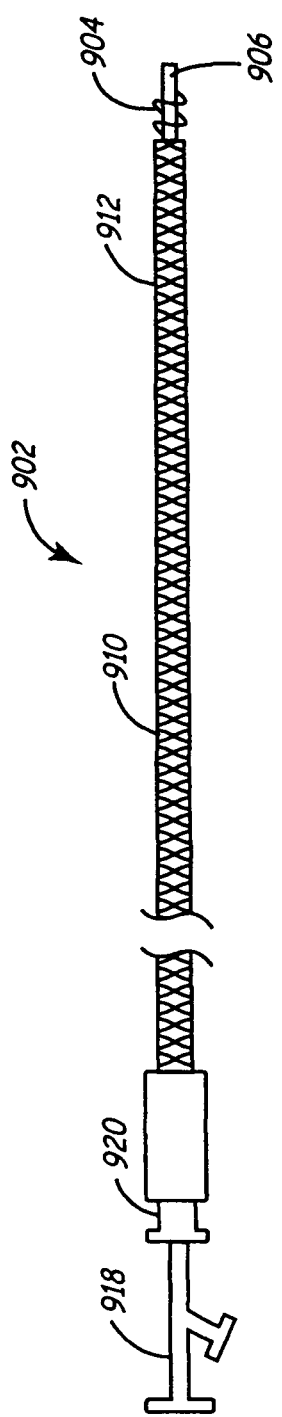
FIG. 31 is a plan view of a delivery catheter or cannula that may be used for accessing the pericardial space through right ventricular apex.
Figure 32:
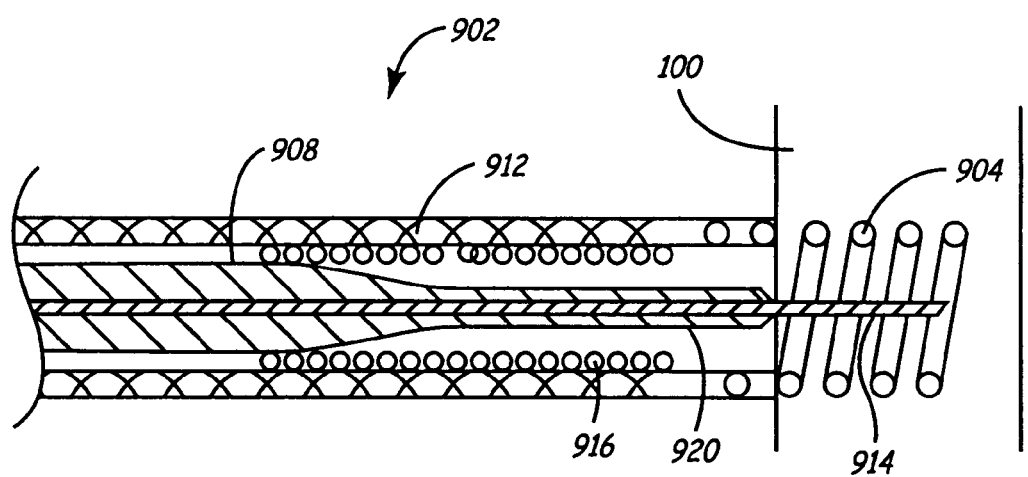
FIG. 32 is an exploded, cut-away view of the distal end of the catheter of FIG. 31 after it has been fixed at an endocardial site.

FIGS. 31 and 32 illustrate a delivery system that may be used for placing an elongated medical device in the pericardial space by passing the medical device through a pericardial access created through the myocardium of the heart wall of a heart chamber, particularly a pericardial access through the right ventricular apex. Implantable medical devices may be more easily positioned over the area or site of the left ventricle by accessing the pericardial space via the pericardial access through the right ventricular apex, thereby eliminating the need for a thorocotomy or other surgical access through the thorax. Such implantable medical devices include fluid delivery catheters for drug or diagnostic fluid delivery or electrical medical leads, e.g., pacing and/or cardioversion defibrillation leads and electrophysiological mapping and/or ablation catheters. Defibrillation thresholds can be significantly reduced when a defibrillation electrode of an elongated defibrillation lead is extended through the pericardial access and placed over the left ventricular free wall. Pacing of left heart chambers can be advantageously accomplished by advancing pacing leads through the pericardial access and locating pace/sense electrodes at selected sites of the left ventricular or atrial epicardium.

FIG. 31 is a plan view of an elongated tubular delivery device 902, e.g. a delivery catheter or cannula, which may be used in the formation of the pericardial access for accessing the pericardial space and an obdurator or leader 906 that is used during advancement of the tubular delivery device 902 transvenously into a heart chamber from a skin incision. Preferably, elongated tubular delivery device 902 is a catheter provided with an elongated tubular catheter body 910 that is provided with a fitting 920 at its proximal end, which may take the form of a Luer lock fitting. Catheter body 910 is preferably formed from a biocompatible polymer, such as polyurethane, a fluoropolymer, or silicone, and is preferably reinforced by an embedded braiding. Embedded braiding is preferably stainless steel, or a high strength polymer fiber such as polyester or nylon. Braided tubular bodies are known in the art, for example, as described in U.S. Pat. No. 5,713,867 issued to Morris, incorporated herein by reference in its entirety. A distal section 912 of the catheter body 910 is provided with greater flexibility than the remainder of the catheter body 910. Greater flexibility of the distal section 912 is provided to reduce the end loading force imposed by the tip of the catheter 902 when it is placed against the endocardium in order to minimize any injury or damage to the endocardial tissue. Distal section 912 may be formed from a lower durometer material than the remainder of catheter body 910.

A fixation member 904 extends from the distal end of the catheter 902. Fixation member 904 is shown as a fixation helix that may correspond generally to fixation member 746 shown in FIG. 28. Fixation member 904 is used to fix the catheter 902 in position against the endocardium and may additionally function as an electrode coupled to a conductor as described above and shown in FIG. 28. Fixation member 904 may alternatively be provided as a barb, suction device, adhesive, or other appropriate fixation mechanism.

A leader 906 is shown exiting the distal end of fixation member 904 with its proximal end 918 entering the proximal end of fitting 920. Leader 906 acts to lead catheter 902 as it is advanced through a venous pathway into the right ventricle. Leader 906 prevents helical fixation member 904 from piercing or snagging on venous or cardiac structures along the way, thereby preventing fixation member 904 from causing unintentional tissue damage as catheter 902 is advanced. Leader 906 preferably takes the form of a steerable diagnostic catheter that allows electrophysiological measurements to be made to confirm placement of the catheter at a desired endocardial site. In an alternative embodiment, leader 906 may take the form of a thin-walled, pliant, polymeric, tubular sheath that extends from the distal end of catheter 902 over the outer diameter of fixation member 904. As fixation member 904 is advanced into the myocardium, the pliant polymeric sheath would be pushed back toward the distal end of catheter 902, allowing unhindered advancement of member 904.

FIG. 32 is an exploded, cut-away view of the distal end of catheter 902 after it has been fixed at an endocardial site using fixation member 904. Fixation member 904 is advanced or screwed into the myocardial wall 100 by rotating the catheter body 910 at its proximal end. The embedded braiding in catheter body 910 provides torsional strengthening that transfers torque applied at the proximal end of catheter 902 to the distal fixation member 904.

In FIG. 32, leader 906 has been removed from the lumen of catheter 902 and replaced with a pericardial access device that includes dilator 908 and an epicardial access device or puncturing device 914. Puncturing device 914 may take the form of a stylet or guidewire having a beveled or sharpened tip in order to puncture through the myocardium of the heart wall and extend into the pericardial space. A puncturing device may alternatively be provided as a needle or coring device, or any device suitable for piercing through the myocardium. Puncturing device 914 is passed through the lumen of dilator 908. Dilator 908 is sized such that its outer diameter fits within the inner diameter of catheter 902 and so that it may be easily advanced or withdrawn through catheter 902. The inner diameter of dilator 908 is sized such that puncturing device 914 may easily pass through the lumen of dilator 908. The wall thickness at the distal end 920 of dilator 908 is preferably reduced such that dilator 908 possesses a small profile at its distal end.

In use, dilator 908 and puncturing device 914 are advanced to the endocardial surface after fixation catheter 902 is positioned at a desired location. Dilator 908 provides stiffening support to puncturing device 914 so that puncturing device 914 may be advanced forward to pierce through the myocardial wall 100, and disposes the puncturing device 914 substantially in axial alignment with the axis of the catheter 902. In FIG. 32, puncturing device 914 is shown partially advanced through the myocardial wall 100. Once through the myocardial wall 100, the puncturing device 914, no longer being constrained by dilator 908, lacks the stiffness to pierce through the relatively tougher pericardium. Dilator 908 may then be advanced through the myocardium into the pericardial space over puncturing device 914. The tip of dilator 908 may be tapered or beveled to ease the process of advancing dilator 908 through the myocardium. The small profile at the distal end 920 of dilator 908 also eases the process of advancing dilator 908 through the myocardium, reducing the size of the myocardial puncture.

With the catheter 902 still fixed over the myocardial puncture, various medical devices may be introduced into the pericardial space through the created pericardial access. The medical devices can be advanced from the skin incision through the lumen of the dilator 908 or through the catheter lumen if the dilator 908 and puncturing device 914 are removed or over the puncturing device 914 left extending through the pericardial access after withdrawal of the dilator 908. For example, an over-the-wire pacing, sensing, or defibrillation lead may be advanced over puncturing device 914, after removing dilator 908. Fluids or other medical devices as described above may be delivered through dilator 908. A diagnostic catheter may be inserted to perform electrophysiological mapping of the left ventricular free wall so that an optimal location for a left ventricular lead may be determined.

In each of these cases and in others, an elongated medical device adapted to be advanced over a wire can be inserted through the delivery device lumen and through the pericardial access over the puncturing device 914 after removal of the dilator 908. In certain cases, it may be possible to also detach and withdraw the catheter 902, so the elongated medical device can be advanced over the puncturing device 914 and through the pericardial access into the pericardial space.

Elongated medical devices having sufficient pushability can also be simply advanced through the delivery device lumen and the pericardial access aligned with it after removal of the puncturing device 914 and the dilator 908 from the delivery device lumen.

The catheter delivery system shown in FIGS. 31 and 32 has been described with regard to accessing the pericardial space via the right ventricle. It is further contemplated that the system described above may be used to access the pericardial space via the left ventricle, for example by introducing the catheter through the femoral artery and guiding the catheter into the left ventricle. The delivery system shown in FIGS. 31 and 32 is also contemplated for use in accessing the interior of the left heart chambers via a septal puncture. Catheter 902 may be fixed on the septal wall of the right ventricle or right atrium and puncturing device 914 and dilator 908 may be advanced through the septum into the left chambers of the heart.

While the present invention is directed primarily toward access to the pericardial space, it is believed that the devices illustrated and describe herein may also usefully be employed to access other portions of the body, particularly spaces within or between other body organs and more particularly to spaces which need to be accessed by penetrating a layer or wall of body tissue. As such, it should be understood that the devices which are the subject of the following claims are not necessarily limited in use to pericardial access.

In conjunction with the above specification,

We claim:

1. An apparatus for delivering fluid to a desired location within a patient's body, comprising:

an elongated outer tubular body having proximal and distal ends, the outer tubular body having a lumen extending from the proximal end to the distal end with an inner surface provided with inwardly directed projections spaced from one another around the circumference of the lumen and defining recesses between them;

an elongated inner tubular member coaxially nested within the lumen of the outer tubular body to longitudinally move and rotate therein, wherein the elongated inner tubular member coaxially nested within the lumen of the elongated outer tubular body extends in a proximal direction beyond the proximal end of the elongated outer tubular body and extends in a distal direction beyond the distal end of the elongated outer tubular body, the inner tubular member having a lumen to receive a fluid delivery catheter and an outer surface provided with outwardly directed projections spaced from one another around the circumference of the inner tubular member and defining recesses between them;

a locking mechanism comprising the inwardly directed projections of the outer tubular body and the outwardly directed projections of the inner tubular member, wherein in a first rotational position of the inner tubular member relative to the outer tubular body, the inwardly and outwardly directed projections and the defined recesses permit the inner tubular member to longitudinally move within the lumen of the outer tubular body and, in a second rotational position of the inner tubular member relative to the outer tubular body, the inwardly and outwardly directed projections are caused to engage one another in an interlocking relationship to prevent longitudinal movement of the inner tubular member within the lumen of the outer tubular body;

a first frustoconical flange carried at a distal end of the elongated inner tubular member; and a second frustoconical flange carried at the distal end of the elongated outer tubular body, said second flange being oppositely directed from said first flange; and a fluid delivery catheter slidably located within the lumen of the inner tubular member, having proximal and distal ends and provided with laterally directed fluid delivery ports adjacent its distal end, the distal end of the fluid delivery catheter being locatable within the inner tubular member.

2. The apparatus of claim 1, wherein the elongated outer tubular body and inner tubular member are adapted to provide access to and delivery of treatment in the pericardial space.

3. The apparatus of claim 1, wherein the inwardly directed projections are spaced apart approximately 120° from one another, the outwardly directed projections are spaced apart approximately 120° from one another, and the inner tubular member is rotated approximately 60° relative to the outer tubular body between the first and second rotational positions.

4. The apparatus of claim 1, wherein the inwardly directed projections on the lumen of the outer tubular body are circumferentially aligned to fond a ring and the outwardly directed projections on the inner tubular member are circumferentially aligned to form a ring.

5. The apparatus of claim 1, wherein the inner lumen surface of the outer tubular body is provided with a plurality of rings of inwardly directed projections, each ring comprising a plurality of projections spaced from one another around the circumference of the lumen and defining recesses between them; and wherein the outer surface of the inner tubular member is provided with a plurality of rings of outwardly directed projections, each ring comprising a plurality of projections spaced from one another around the circumference of the inner tubular member and defining recesses between them.

* * * * *